United States Patent
Velleu et al.

(10) Patent No.: US 11,568,577 B2
(45) Date of Patent: Jan. 31, 2023

(54) CONTAMINATION DETECTION AND NOTIFICATION SYSTEMS

(71) Applicant: GM GLOBAL TECHNOLOGY OPERATIONS LLC, Detroit, MI (US)

(72) Inventors: Jesse Velleu, Ann Arbor, MI (US); Omer Tsimhoni, Bloomfield Hills, MI (US); John Phillips, Macomb, MI (US)

(73) Assignee: GM GLOBAL TECHNOLOGY OPERATIONS LLC, Detroit, MI (US)

( * ) Notice: Subject to any disclaimer, the term of this patent is extended or adjusted under 35 U.S.C. 154(b) by 6 days.

(21) Appl. No.: 17/118,893

(22) Filed: Dec. 11, 2020

(65) Prior Publication Data

US 2022/0189072 A1 Jun. 16, 2022

(51) Int. Cl.
| | |
|---|---|
| G09G 5/00 | (2006.01) |
| G06T 11/00 | (2006.01) |
| H04W 4/029 | (2018.01) |
| H04N 5/232 | (2006.01) |
| H04N 9/31 | (2006.01) |
| H04W 4/48 | (2018.01) |
| G06V 20/59 | (2022.01) |

(52) U.S. Cl.
CPC .............. *G06T 11/00* (2013.01); *G06V 20/59* (2022.01); *H04N 5/23293* (2013.01); *H04N 9/3173* (2013.01); *H04W 4/029* (2018.02); *H04W 4/48* (2018.02)

(58) Field of Classification Search
CPC ....... G06T 19/006; G06T 19/00; G06F 3/011; G06F 3/012; G02B 27/017
USPC .......................................................... 345/633
See application file for complete search history.

(56) References Cited

U.S. PATENT DOCUMENTS

| | | | | |
|---|---|---|---|---|
| 2010/0117836 | A1* | 5/2010 | Seyed Momen | G16H 40/20 340/573.1 |
| 2019/0091738 | A1* | 3/2019 | Chen | B60H 1/00742 |
| 2020/0279642 | A1* | 9/2020 | Lee | G16H 40/20 |
| 2021/0188541 | A1* | 6/2021 | Kurani | B65F 1/1484 |

OTHER PUBLICATIONS

U.S. Appl. No. 17/118,933, filed Dec. 11, 2020, Mathieu et al.

* cited by examiner

*Primary Examiner* — Gordon G Liu

(57) ABSTRACT

A notification system includes a memory, an output device and activity, localization, and tracking modules. The memory stores an activity history log associated with a supporting structure. The activity module: receives signals from sensors or electrical devices; and tracks activities at least one of in or within a set distance of the supporting structure to generate the activity history log. The localization module relates the activities to aspects of the supporting structure and generates corresponding localization data. The tracking module tracks states of the aspects of the supporting structure contacted at least one of directly or indirectly by one or more animate objects and determine at least one of contamination levels or sanitization levels of the aspects based on the localization data and the activity history log. The output device indicates the at least one of the contamination levels or the sanitization levels.

20 Claims, 6 Drawing Sheets

CONTAMINATION DETECTION AND NOTIFICATION SYSTEMS

INTRODUCTION

The information provided in this section is for the purpose of generally presenting the context of the disclosure. Work of the presently named inventors, to the extent it is described in this section, as well as aspects of the description that may not otherwise qualify as prior art at the time of filing, are neither expressly nor impliedly admitted as prior art against the present disclosure.

The present disclosure relates to surface and interior space contamination detection systems.

Contaminants may be spread by common touchpoints of a vehicle, a building, and/or other supporting structure. For example, an occupant of a vehicle that is sick and/or has, for example, a virus may contact various points on and/or in a vehicle, such as door handles, armrests, seats, switches, steering wheel, etc. The occupant may also, through the air, contaminate surfaces by breathing, coughing, and/or sneezing within the vehicle. This can result in the spread of germs onto surfaces within the vehicle. A second occupant may contact the same surfaces and/or breathe in contaminated air within the vehicle and as a result become infected.

As another example, a first individual that is sick and/or has been exposed to a virus may stay as a guest in a hotel room and contact various surfaces of the hotel room. A second individual may reserve and stay in the same hotel room subsequent to the first individual. During the second individual's stay in the hotel room, the second individual may contact contaminated surfaces that were not adequately cleaned and as a result contract the virus. This may similarly occur when a hotel staff member exposed to a virus enters and/or cleans a hotel room. The hotel staff member may contaminate surfaces by physical contact and/or by spreading of contaminated droplets while breathing, coughing and/or sneezing in the hotel room. A guest subsequently staying in the hotel room may then contract the virus.

SUMMARY

A notification system is provided and includes a memory, an activity module, a localization module, a tracking module and an output device. The memory is configured to store an activity history log associated with a supporting structure. The activity module is configured to: receive signals from at least one of sensors or electrical devices of the supporting structure; and track activities at least one of in or within a set distance of the supporting structure to generate the activity history log. The localization module is configured to relate the activities to aspects of the supporting structure and generate corresponding localization data. The aspects include at least one of surfaces, areas, spaces or volumes of the supporting structure. The tracking module is configured to track states of the aspects of the supporting structure contacted at least one of directly or indirectly by one or more animate objects and determine at least one of contamination levels or sanitization levels of the aspects based on the localization data and the activity history log. The output device is configured to indicate the at least one of the contamination levels or the sanitization levels.

In other features, the notification system further includes a transceiver configured to receive a notification key indicating a network device has been identified as being exposed to a contaminant. The tracking module is configured to, in response to the notification key, track the aspects of the supporting structure contacted by the one or more animate objects and determine the at least one of the contamination levels or the sanitization levels of the aspects based on the localization data and the activity history log.

In other features, the notification system further includes the sensors configured to detect activities in the supporting structure. The activity module is configured to track the activities based on outputs of the sensors.

In other features, the notification system further includes the electrical devices configured to change state as a result of activities in the supporting structure, where the activity module is configured to track states of the electrical devices and log the states in the activity history log.

In other features, the supporting structure is a vehicle. The output device is at least one of a display of the vehicle or one or more smart aspects of the vehicle.

In other features, the notification system further includes one or more cameras configured to track activities of the one or more animate objects. The activity module is configured to determine aspects of the supporting structure contacted based on outputs of the one or more cameras and log the aspects contacted and corresponding timestamps in the activity history log.

In other features, the activity module is configured to track touch points of the one or more animate objects and log the touch points and corresponding timestamps in the activity history log.

In other features, the output device is at least one of a display or a projector. The output device is configured to at least one of: highlight areas of the supporting structure in an image shown on the display to illustrate the at least one of the contamination levels or the sanitization levels of the aspects; or project images on the aspects of the supporting structure to indicate the at least one of the contamination levels or the sanitization levels of the aspects.

In other features, the tracking module is configured to identify aspects contacted based on activities performed and update the at least one of the contamination levels or the sanitization levels based on the identified aspects contacted.

In other features, the tracking module is configured to identify aspects contacted based on detected changes in states of the electrical devices and update the at least one of the contamination levels or the sanitization levels based on the identified aspects contacted.

In other features, the notification system further includes sensors configured to detect at least one of breathing, coughing or sneezing by the one or more animate objects. The tracking module is configured to, based on the detected at least one of the breathing, coughing or sneezing, update the at least one of the contamination levels or the sanitization levels.

In other features, the activity module is configured to track number of times each of the aspects are contacted and durations of contacts with the aspects. The tracking module is configured to update the at least one of the contamination levels or the sanitization levels based on the number of times each of the aspects are contacted and the durations of the contacts with the aspects.

In other features, the tracking module is configured to update the at least one of the contamination levels based on decay rates associated with materials of the aspects.

In other features, the notification system further includes a transceiver configured to transmit the activity history log to a server and receive in response a cleaning notification message indicating at least one of areas or aspects of the supporting structure to sanitize.

In other features, the activity module performs motion tracking of the animate objects and determines incidents in which physical contact is made with interior aspects of the supporting structure and updates the activity history log based on the physical contacts made.

In other features, the notification system further includes embedded sensors configured to detect contact with the aspects. The activity module is configured to update the activity history log based on outputs of the embedded sensors.

In other features, a portable network device is provided and includes a camera, a memory and a control module. The camera is configured to capture images of a supporting structure. The memory is configured to store localization data, where the localization data relates location and orientation of the portable network device to aspects of the supporting structure, where the aspects include at least one of surfaces, areas, spaces or volumes of the supporting structure, and where the supporting structure is separate from the portable network device. The control module is configured to: receive at least one of (i) an activity history log of activity of one or more animate objects in association with the supporting structure, (ii) a contamination map of contamination levels of aspects of the supporting structure, or (iii) sanitization map of sanitization levels of aspects of the supporting structure; and based on the captured images, display an image of the supporting structure indicating at least one of the contamination levels of the aspects or the sanitization levels of the aspects.

In other features, the displayed image is updated for different areas of the supporting structure as the location and orientation of the portable network device changes.

In other features, the control module is configured to highlight the aspects based on the at least one of the contamination levels of the aspects or the sanitization levels of the aspects in an augmented reality environment view of the supporting structure.

In other features, the portable network device further includes a view-finder module configured to determine a relationship between a live view seen by the camera and the at least one of the contamination map or the sanitization map. The control module is configured to operate in an augmented reality mode and provide a view of an interior of the supporting structure highlighting the aspects in the view based on the at least one of the contamination levels of the aspects or the sanitization levels of the aspects.

Further areas of applicability of the present disclosure will become apparent from the detailed description, the claims and the drawings. The detailed description and specific examples are intended for purposes of illustration only and are not intended to limit the scope of the disclosure.

BRIEF DESCRIPTION OF THE DRAWINGS

The present disclosure will become more fully understood from the detailed description and the accompanying drawings, wherein.

In the drawings, reference numbers may be reused to identify similar and/or identical elements.

DETAILED DESCRIPTION

Figure 1:
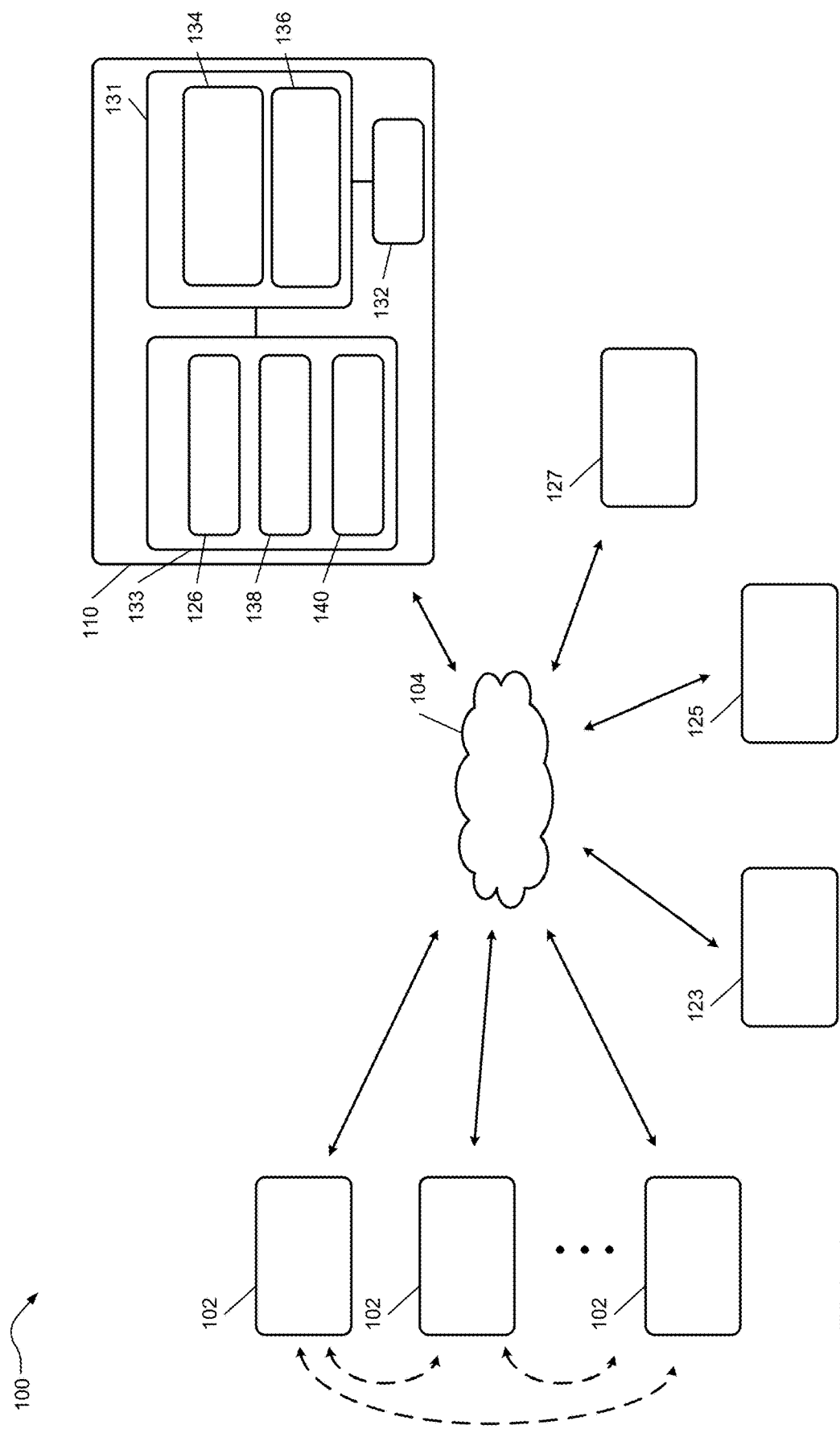
FIG. 1 is a functional block diagram of an example of a contamination detection and notification system in accordance with the present disclosure.

Locating contaminated areas can be difficult. It can be unclear what surfaces have been contacted and/or require sanitization and/or avoidance so as not to catch a virus and possibly become sick. For example, it can be difficult to determine which surfaces within a vehicle are contaminated. Also, cleaning interiors of a vehicle, a room, a building, etc., can be inefficient without knowing (i) which specific areas are contaminated and/or need cleaning, and (ii) which areas are not contaminated and do not need cleaning.

The examples set forth herein include contamination detection and indication systems. The systems indicate surface areas that are contaminated and/or surfaces areas that have been sanitized. This allows for easy detection and avoidance of these areas and/or identification of contaminated areas for cleaning purposes. In a vehicle environment, the systems detect and provide views of vehicle interiors with indications of areas touched by previous passengers in order to identify likely areas of contamination. Sensors and other component state detection operations are performed concurrently and non-invasively to track where interior vehicle surfaces have been contacted. In some embodiments, the systems display a contamination mapping and/or sanitization mapping highlighting contaminated areas and/or sanitized areas. This information may be provided in the form of an augmented reality (AR), where for example, a display of a portable network device shows an interior area including highlighted portions indicating areas that are contaminated and/or sanitized. This is further described below. The examples include performing countermeasures to decontaminate the surfaces and prevent further contamination and/or spread of germs to other users, occupants, customers, etc.

Contamination levels of surfaces can decay over time and may be based on whether contacted surfaces are anti-microbial and/or anti-viral surfaces. An anti-microbial surface includes an anti-microbial agent that inhibits the ability of microorganisms to grow. Similarly, an anti-viral surface includes an anti-viral agent that inhibits the ability of a virus to grow, live and/or spread. As an example, an anti-microbial surface and an anti-viral surface may include copper and/or a copper alloy, which are both anti-microbial and anti-viral materials. The decay rate refers to the rate at which microorganisms and/or viral organisms die off when exposed to the anti-microbial and anti-viral surface materials.

Contamination levels may also based on direct or indirect contact with surfaces. Direct contact may refer to when a person identified as having been exposed to a contaminate physically contacts and/or touches a surface, an inanimate object and/or an animate object. Indirect contact may refer to when the person breathes, coughs and/or sneezes on or near a surface. Indirect contact may also refer to when a second individual contacts a surface contacted by the person identified as having been exposed and/or entering a space where the exposed person was previously. Indirect contact by the second individual can occur through physical contacts with surfaces and/or through the air. Although below examples are primarily described with respect to contamination and sanitization levels of surfaces, other aspects such as areas, spaces and/or volumes of supporting structures may also be monitored and tracked. Countermeasures may be performed based on contamination and sanitization levels of any of these aspects.

Although some of the below described embodiments are directed to vehicular applications, the described embodiments are also applicable to other non-vehicular applications. For example, the embodiments are applicable to hotels, elevators, doorways, restrooms, banks, automatic teller machines (ATMs), stores, food markets, private residences, businesses, restaurants, public transportation, vending machines, operating rooms and equipment, etc. The embodiments are applicable to automotive vehicles, trains, subways, airplanes, watercraft and/or other vehicles.

FIG. 1 shows a contamination detection and notification system 100 that includes network devices 102, a distributed network 104 and a central monitoring station 110. The network devices 102 may include network devices within vehicles, buildings, rooms, and/or other supporting structures. The network devices 102 may include, for example, telematics modules, infotainment modules, control modules, etc. of various devices and/or vehicles. The network devices 102 may further include portable network devices, such as cellular phones, mobile access devices, tablets, laptop computers, wearable devices, smart glasses, virtual reality devices (e.g., virtual reality headsets), etc. The network devices may be directly in communication with each other or indirectly via the distributed network 104. The distributed network 104 may include local area networks (LANs), wireless local area networks (WLANs), cellular networks, etc. The distributed network 104 may include routers, modems, satellites, base stations, gateways, etc.

The central monitoring station 110 may be associated with a vehicle manufacturer and/or a service provider, such as a car rental or leasing company, a rideshare service company, a car service station, and/or other service provider. The central monitoring station 110 may include a control module 131, a transceiver 132 and memory 133. The control module 131 may include a contamination and sanitization tracking module 134 and a cleaning indication module 136. The contamination and sanitization tracking module 134 may track and/or evaluate data in the activity history log 126, contamination data 138, and/or sanitization data. The contamination and sanitization tracking module 134 may perform a more detailed data analysis and/or localization mapping than that performed at the network devices 102 and share the results with the network devices 102. Localization mapping is further described below. The localization mapping may (i) relate contact points to contamination levels and/or sanitization levels, and/or (ii) relate location and orientation of network devices to supporting structures and corresponding surfaces.

The cleaning indication module 136 may provide suggested cleaning instructions as further described below based on the activity history log 126, contamination data 138, sanitization data and/or results of the analysis performed by the contamination and sanitization tracking module 134. The memory 133 may store the activity history log 126, contamination data 138 and sanitization data 140.

The central monitoring station 110 may store activity data received from the network devices 102 in the form of the activity history log 126. The activity history log 126 may include a list of activities that have occurred over time, where each activity includes an activity identifier, a timestamp (including a date and time), and a duration over which the activity occurred. As an example, various activities may occur in and/or in association with a vehicle. The activities may include: opening and closing doors; opening and closing windows; activating and deactivating lights, entertainment equipment, stereos, an air-conditioning system; adjusting seat and mirror positions; adjusting steering angles; adjusting temperatures of seats; adjusting positions of seats; etc. All of these activities include a vehicle occupant contacting various surfaces, such as door handles, control knobs, steering wheel, buttons, switches, mirrors, armrests, seats, dashboards, consoles, dashboards, cup holders, etc. This contacting can transfer germs as described above to the surfaces and/or from the surfaces to the occupant. The activity history log 126 may be a rolling log that includes data for a last predetermined period of time (e.g., 14 days).

Figure 5:
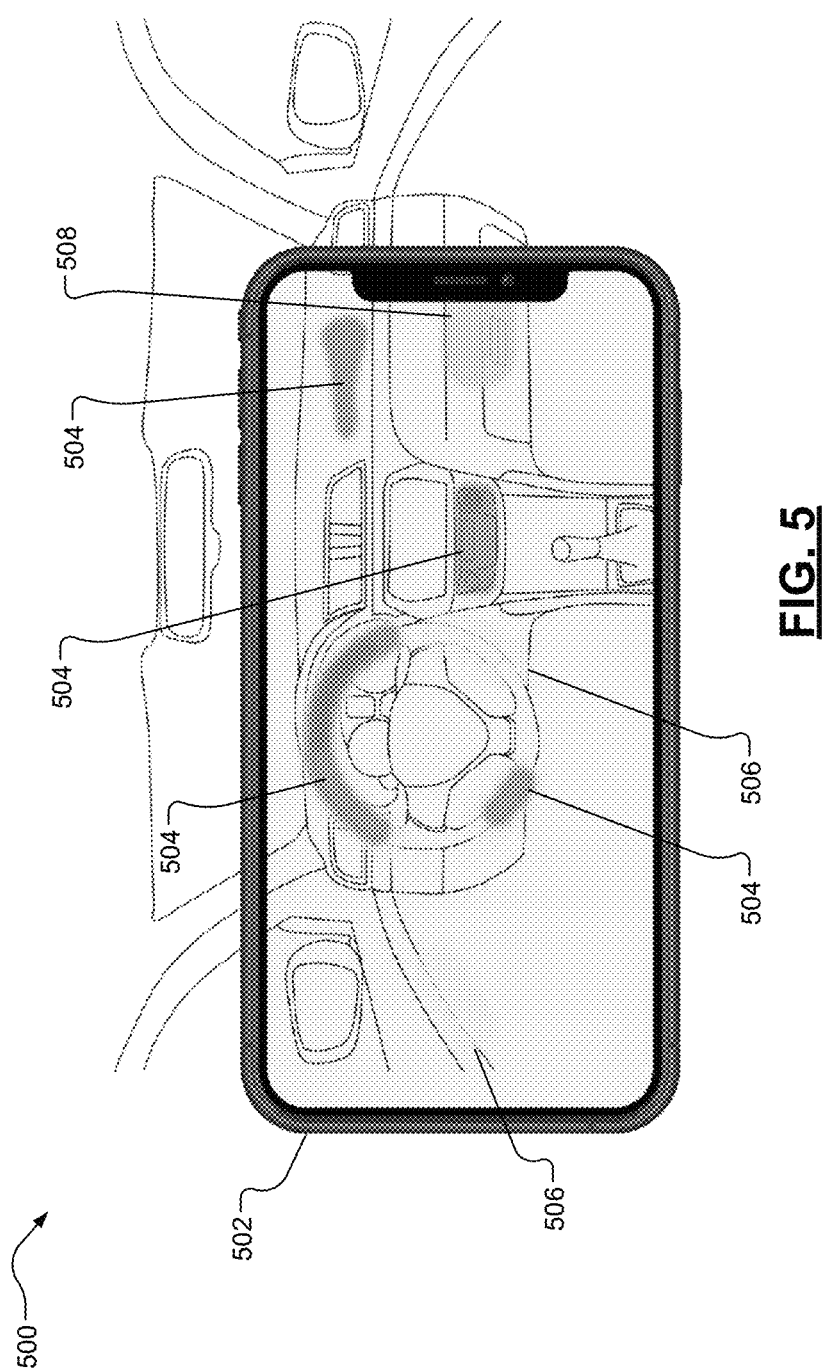
FIG. 5 is forward facing perspective view of an example of an interior of a vehicle illustrating an augmented reality view via a portable network device in accordance with the present disclosure.

The contamination data (or contamination mapping data) 138 may include data that indicates levels of contamination for various surfaces, for example, within a supporting structure and related to locations on a map of the supporting structure. The contamination data 138 may be displayed in an overlapping manner, for example, over an image (or view) of an area. An example illustration is shown in FIG. 5. A similar mapping including levels of sanitization may be provided for the sanitization data (sanitization mapping data) 140. This information may be reported to the occupant via displays and/or an audio system within the vehicle and/or via one or more of the network devices 102.

As an example, the control module 131 may report contamination levels and/or sanitization levels of surfaces of numerous vehicles monitored by a fleet manager. The control module 131 and/or the fleet manager may then send signals to vehicle drivers to clean surfaces of the vehicles. The control module 131 and/or the fleet manager may indicate which surfaces need to be cleaned and which surfaces may not need to be cleaned based on collected data.

The contamination detection and notification system 100 may further include sensors 123, indicator input devices 125, and output devices 127. The sensors 123, indicator input devices 125, and/or output devices 127 may be located at and/or in close proximity to the network devices 102 and/or a supporting structure. The sensors 123 and/or output devices 127 may be implemented as part of the network devices 102 and/or supporting structures. The sensors 123 and/or output devices 127 may be implemented separate from the network devices 102 and/or supporting structures. The sensors 123 may include position sensors, contact sensors, pressure sensors, weight sensors, location sensors, linear sensors, rotary sensors, potentiometers, piezoresistive sensors, load sensors, piezoelectric sensors, cameras, infrared sensors, Lidar sensors, radar sensors, air flow sensors, microphones, surface embedded sensors, force sensors, etc. The sensors 123 may include window position sensors, door position sensors, mirror position sensors, steering sensors and/or other position sensors. The sensors 123 may be located on or in network devices, supporting structure, and and/or nearby infrastructure (such as traffic poles, traffic signals, bridges, walls, etc.). The sensors 123 may be used to detect the presence of occupants and register them. The sensors 123 may be used to identify user interactions with vehicle surfaces based on historical human-vehicle interaction activities (entry, egress, switch operation, etc.).

The indicator input devices 125 may include switches, knobs, slides, dials, motors, actuators, transceivers, touch screens, touch pads, buttons, etc. The output devices 127 may include displays, screens, lights, mirrors, wiper motors, gear shifters, electrical steering devices, audio devices (e.g., speakers), smart surfaces, and/or other electrical devices. Smart surfaces in the context of this disclosure refer to surfaces that are able to physically change in state, such as in color and/or shade. The different colors and/or shades may be associated with different contamination and/or sanitization levels. Smart surfaces may be able to display information to indicate contamination and/or sanitization levels. In another embodiment, the output devices 127 include directional lights and/or light emitting diodes (LEDs) that are controlled and able to light up different areas using different colors and/or illumination patterns. The lights may be strobed at different frequencies. As an example, a dome light housing in a vehicle may have any number of LEDs that are controlled to indicate levels of contamination and/or sanitization on surfaces within the vehicle.

As an example, the sensors 123, the indicator input devices 125 and output devices 127 may be located throughout a vehicle. The sensors and indicator input devices 125 may be used to monitor and track contact activity associated with the vehicle. As an example, cameras may be used to monitor the interior of a vehicle and detect surfaces that have been touched and/or contacted, number of times contacted, and the lengths of each contact. This information may be timestamped for contamination and sanitization based determinations. This type of contact activity is recorded and may be reported by one or more of the network devices 102 to the central monitoring station 110.

The network devices 102 may indicate the contamination and/or sanitization levels of the surfaces via devices of the vehicle and/or via portable network devices located in the vehicle. The central monitoring station 110 may use the received activity information to determine contamination and/or sanitization levels of surfaces. The contamination and/or sanitization levels and/or alert information may be generated by the control module 131 and transmitted back to the network devices 102. The alert information may indicate the stated levels, areas to sanitize, areas that have been sanitized, areas that have unknown (or undeterminable) contamination and sanitization levels, areas that have not been contacted for extended periods of time, etc.

Figure 2:
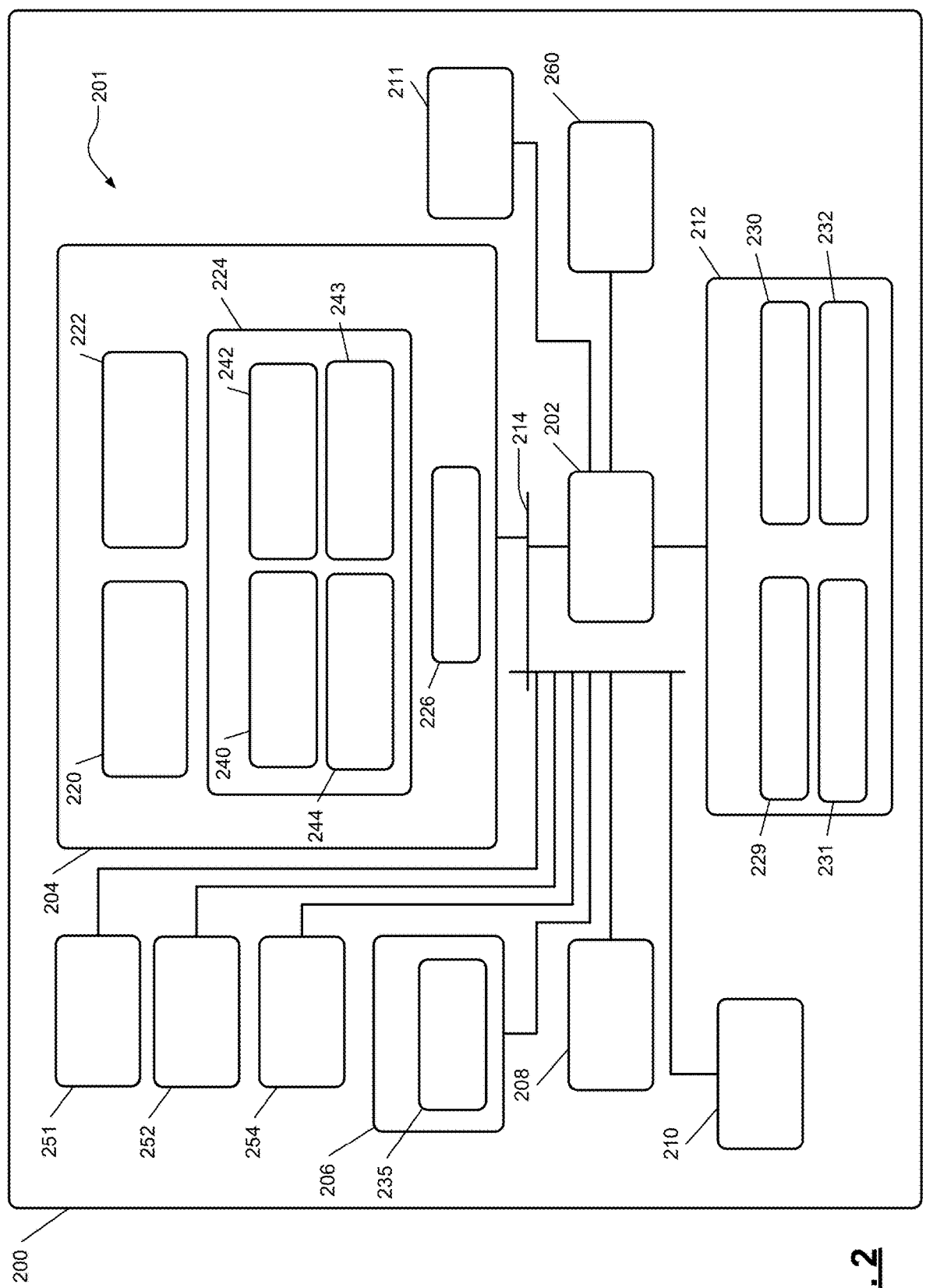
FIG. 2 is a functional block diagram of an example of a supporting structure including modules for contamination, sanitization and activity tracking in accordance with the present disclosure.

FIG. 2 shows a supporting structure 200 including a contamination detection and notification system 201 that includes a control module 202, an infotainment module 204, a telematics module 206, indicator input devices 208, sensors 210, output devices 211 and a memory 212. The supporting structure 200 may be a vehicle, a building, a room, a machine, or other supporting structure. The control module 202 may be a central (or main) control module of the supporting structure. For example, if the supporting structure 200 is a vehicle, the control module 202 may be a body control module or other vehicle control module. The infotainment module 204, the telematics module 206, the indicator input devices 208 and the sensors 210 may be connected to the control module 202 via a controller area network (CAN) bus 214.

The infotainment module 204 may include a contamination tracking and indication module 220, a sanitization tracking and indication module 222, an activity tracking module 224 and a localization module 226. The modules 220, 222, 224 may be referred to as tracking modules. The module 224 may be referred to as an activity module. The activity tracking module 224 may include a motion tracking module 240, a physical contact and/or surface module 242 and an air monitoring module 244. Any of these modules may be included in the control module 202. Also, any combination of these modules may be integrated as part of a single module.

The contamination tracking and indication module 220 may monitor, track and/or determine contamination levels of surfaces, such as surfaces of a vehicle, a room, a machine, etc. The contamination tracking and indication module 220 may collect activity data associated with use and/or corresponding localization data to estimate contamination levels based on monitored activities. The tracking may include storing contact times, number of contacts at each location and/or point, durations of contacts, and dates that the contacts occurred. The contamination tracking and indication module 220 may store the contamination levels as contamination data 229 in the memory 212.

The sanitization tracking and indication module 222 may monitor, track and/or determine sanitization levels of surfaces, such as surfaces of a vehicle, a room, a machine, etc. The sanitization tracking and indication module 222 may collect activity data associated with use and/or corresponding localization data to estimate sanitization levels based on monitored cleaning. This tracking may be based on a trigger event, such as the above-stated trigger event. The sanitization tracking and indication module 222 may store the sanitization levels as sanitization data 231 in the memory 212.

The activity tracking module 224 may collect data from the sensors 210 and indicator input devices 208, which may be similar to the sensors 123 and the indicator input devices 125 of FIG. 1. This activity tracking may be based on a trigger event and/or may be continuously tracked. A trigger event may be a request to begin tracking and/or other trigger event. The activity tracking module 224 records over a predetermined period of time activity tracking data 230, which is stored in the memory 212, such as which doors were opened, what windows were actuated, what buttons were pushed, etc. This may include identifying surfaces contacted and determining the length of contacts, number of times contacted, and recording timestamp information including times and dates of contacts. It can be inferred that certain handles, knobs, buttons, and/or other controls have been touched when certain vehicle events occur (e.g., a door opens or closes, a window is actuated, a state of a radio changes, etc.), except for when voice commands are provided. The activity tracking module 224 may refrain from recording activity that is associated with voice commands. When voice activated, a surface may not be touched and thus recording of this type of activity may not be needed. If a button is pushed to activate voice operations, then information associated with pushing the button may be recorded. The facing direction and/or direction of speech may be detected and tracked. Surfaces forward of the speaker may be identified as being in potential contact of the breath of the speaker and/or droplets due to coughing and/or sneezing of the speaker. These determinations may be made based on recorded and analyzed video and/or audio detecting the location and facing direction of the speaker.

The activity tracking module 224 may include a motion tracking module 240, a physical contact and surface module 242, and an air monitoring module 244. Any of these modules may be included in the control module 202. Also, any combination of these modules may be integrated as part of a single module. The activity tracking module 224 may implement a contact tracking application for initiating and tracking contact information, which may be started via, for example, a user tapping on an icon on a display, such as a display included in the output devices 211.

The motion tracking module 240 may execute algorithms to track movement of users, occupants and/or customers within a vehicle, a building or a room. This may be done using cameras and/or other motion tracking equipment to track movement. For example, the motion tracking module 240 may track movement of cleaning staff of a hotel and/or hotel guests based on which doors have been opened, which access cards have been swiped through which card readers, etc. Activity associated with electronic devices such as coffee makers, televisions, refrigerators, hair dryers, irons, computers, thermostats, etc. may be monitored and tracked. This may be implemented to determine in which rooms cleaning staff and/or hotel guests have been. The motion tracking module may also be used to track movement within a vehicle to determine where contacts with surfaces have occurred and/or orientation of occupants within the vehicle. As an example, an occupant of a vehicle may open a door, sit in a certain seat, close the door, use a seat belt, perform certain activities, and then reopen and close the door while leaving the vehicle. All of which may be tracked and recorded. This information may be included in the activity tracking data 230. The physical contact and/or surface module 242 may track which surfaces have be touched and/or contacted based on signals from contact sensors and/or other sensors. This information may also be included in the activity tracking data 230.

The air monitoring module 244 may monitor air quality levels within an enclosed area, such as within a vehicle, a room, etc. This may be based on signals received from sensors, such as air flow sensors, fans, air-conditioning systems, air filtration systems, etc. The air quality level information may also be included in the activity tracking data 230. The air monitoring module 244 may monitor a microphone and/or other sensors to track coughing, sneezing, and/or other sounds implying the spread of germs through the air. This information may be related to images to determine what surfaces have been potentially affected by the transfer of these germs.

The localization module 226 may associate contacts with locations. For example, cameras may be used to capture images and based on the images the localization module is able to identify surfaces contacted and where on the surfaces contacts were made. The localization module 226 may store localization data 232 indicative of the stated locations in the memory 212 and be accessible to the other stated modules.

The above-stated data and information stored in the memory 212 may be generated, received, and/or shared by the modules 204, 220, 222, 224, 226, 240, 242, 244. The supporting structure 200 may include a projector 260, which may be one of the output devices 211. The projector 260 may project an image over surfaces of an area to indicate contamination and/or sanitization levels of the surfaces. In one embodiment, multiple projectors are used to project images over surfaces to indicate contamination and/or sanitization levels. In another embodiment, a simple projector having one or more LEDs are used to project light and highlight one or more areas. As yet another example, a green or red light may be projected onto an internal or external door handle or the handle may include a green or red light to indicate whether the handle has or has not been used.

The memory 212 may store information associated with compound touches between clean and contact events. Although the contamination and contaminate examples referred to herein are primarily described as viral related, the examples are applicable to other contaminates. Time tracking is performed to provide information indicating when viral, chemical, and/or radioactive contaminates have likely decayed.

In one embodiment, the supporting structure 200 includes a cleaning system 251, which may initiate and/or perform cleaning operations based on instructions from the infotainment module 204. This may include, for example, activating an ultraviolet C-bond (UVC) light and/or injecting and/or spraying disinfectant in an area of the supporting structure 200. The cleaning system 251 may include, for example, a UVC light, a reservoir with disinfectant and/or a pump for spraying the disinfectant. The light and the pump may be controlled by a module of the cleaning system 251, the control module 202 and/or other control module. In another embodiment, the supporting structure 200 is an autonomous vehicle and the cleaning system 251 initiates an action to move the vehicle through a cleaning station, such as a car wash. In another embodiment, the cleaning system 251 opens windows 252 and/or runs fans 254 within the interior of the vehicle to air out the interior of the vehicle.

Figure 3:
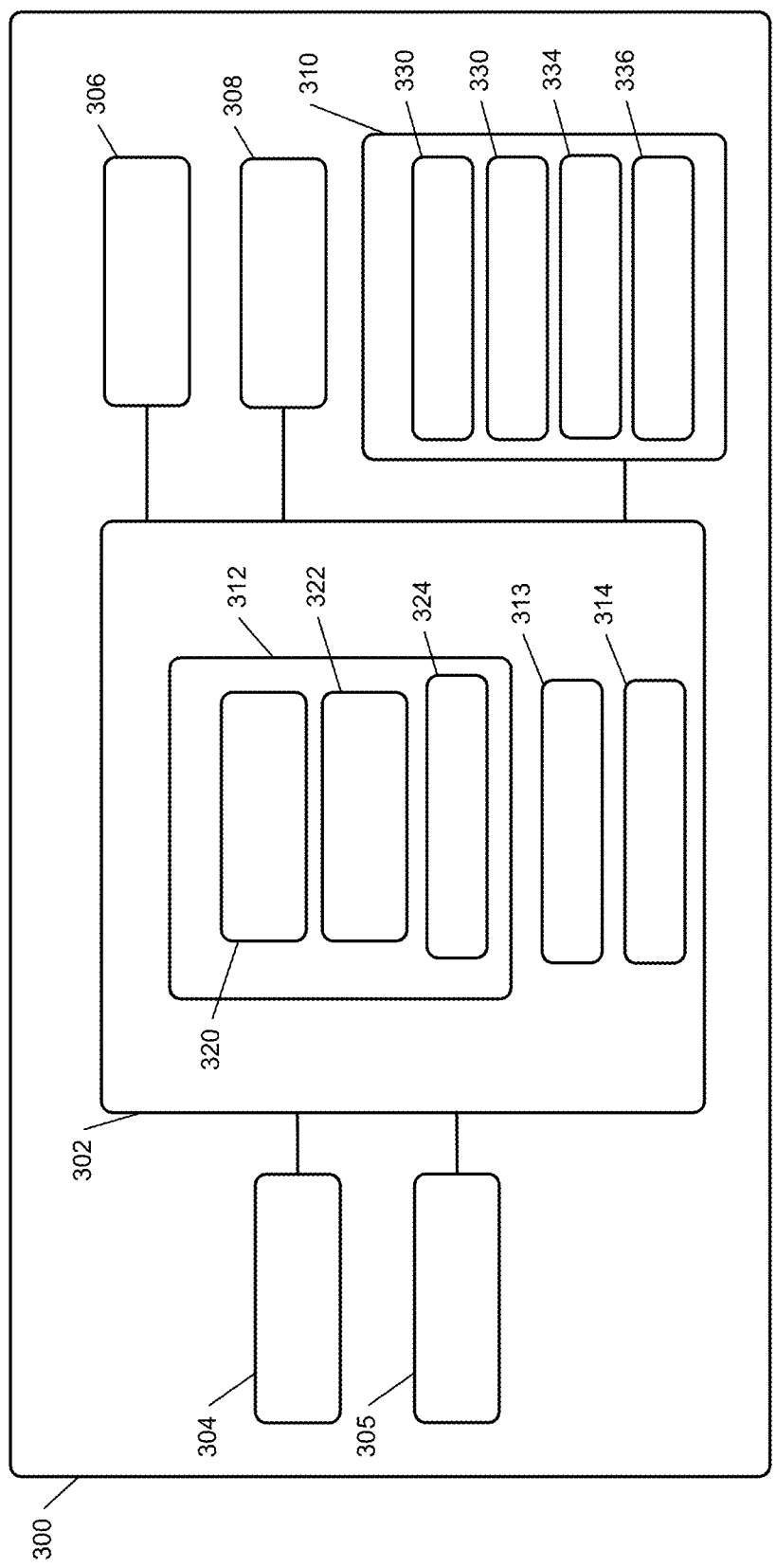
FIG. 3 is a functional block diagram of an example of a portable network device including contamination and sanitization modules in accordance with the present disclosure.

FIG. 3 shows a portable network device 300 including a control module 302, a transceiver 304, sensors 305, a display 306, an audio system 308, and a memory 310. The portable network device 300 may replace any of the network devices 102 of FIG. 1. The portable network device 300 may be a separate network device, such as a mobile phone, a tablet, a wearable device, or may be integrated and/or embedded in a vehicle and/or other supporting structure. The control module 302 may include a view finder module 312, a contact tracking application 313, and/or a cleaning application 314. The applications 313, 314 may be activated via respective icons shown on the display 306.

The view finder module 312 may include a contamination module 320, a sanitization module 322 and/or a localization module 324. The view finder module 312 may determine a location and orientation of the portable network device 300 based on signals from the sensors 305. The sensors 305 may include cameras, global positioning sensors, accelerometers, a gyroscope, etc. Position, location and orientation of the portable network device 300 may be determined by the control module 302 and/or by, for example, one or more of the modules 202, 204, 206 of the supporting structure of FIG. 2 and then shared with the portable network device 300 and/or supporting structure 200. The view finder module, based on the location and orientation, may display contamination and/or sanitization information over a current view seen by one of the cameras. The contamination module 320 may determine the contamination levels of surfaces and/or areas displayed. The sanitization module 322 may determine sanitization levels of surfaces and/or areas displayed. The contamination and sanitization information may be received from a supporting structure and/or a server, such as one of the supporting structures and/or servers of FIGS. 1-2. The localization module 324 may associate the location and the orientation of the portable network device 300 with a surrounding environment and nearby surfaces and/or surfaces in a field of view of the one of the cameras.

The contact tracking application 313 may be used to activate and monitor contamination and/or sanitization levels, which may be indicated via the display 306 and/or the audio system 308. The contact tracking application 313 may be executed along the contact tracking application 243 of FIG. 2. The cleaning application 314 may display cleaning information indicating surfaces and/or areas to clean, areas that have been cleaned, when the areas were last cleaned, surfaces that were last cleaned, when the surfaces were last cleaned, probability levels of whether certain surfaces and/ or areas have been cleaned, etc. FIG. 5 illustrates an example showing contamination levels. The cleaning application 314 may provide similar overlapping images for levels of cleanliness and/or levels of sanitization.

Contamination and sanitization information may be conveyed via the display 306 and/or the audio system 308. The audio system 308 may include a speaker, a headset, and/or other audio device. An application similar to the application 314 may be implemented by the infotainment module 204 of the supporting structure 200 of FIG. 2. For example, this application may be implemented by a network device of a vehicle and convey similar information via a display, a projector, and/or an audio system.

The memory 310 may store contamination data 330, sanitization data 332, localization data 334 and/or cleaning data 336. The stated data may be generated, received, and/or shared by the modules 302, 312, 320, 322.

Figure 4:
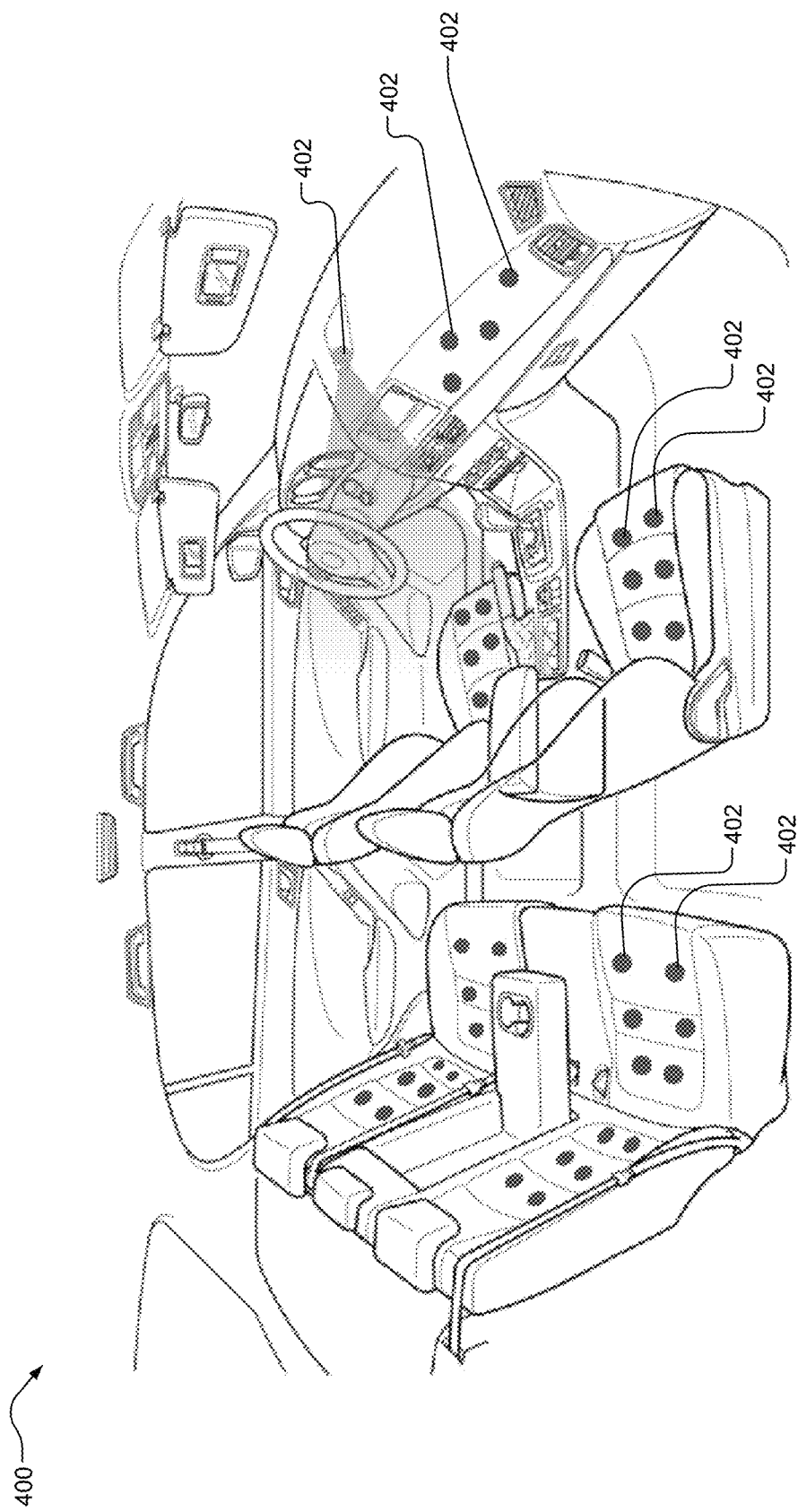
FIG. 4 is a side perspective view of an example of an interior of a vehicle with activity tracking and contact sensors in accordance with the present disclosure.

FIG. 4 shows an interior 400 of a vehicle with activity tracking and contact sensors 402. The activity tracking and contact sensors 402 may include cameras, touch sensors, pressure sensors, etc. The cameras may be located in various locations and track activity. The cameras may include birds-eye cameras, ceiling mounted cameras, cameras mounted on a dashboard and/or a pillar, and/or other cameras. Overhead, front, side, rear and angled camera views may be captured and displayed. The pressure sensors may be located in, for example, seats of the vehicle and detect when an occupant is sitting in a particular seat. The touch sensors may be located in various components, panels, armrests, control actuators (e.g., knobs, buttons, dials, etc.), and/or elsewhere in the vehicle. The touch sensors may detect when an occupant has touched a particular location.

FIG. 5 shows an interior 500 of a vehicle illustrating an augmented reality view via a portable network device 502. The portable network device 502 is held up by a user in front of a vehicle interior to show highlighted touch points. The portable network device 502 may be configured as one of the network devices 102 of FIG. 1 and/or the portable network device 300 of FIG. 3. The portable network device 502 may overlay contamination information on a live view of the interior 500. The user may point the camera of the portable network device 502 in different directions within the interior 500 in order to see the levels of contamination on various interior surfaces.

In the example shown, the contamination information is shown as highlighted areas having different colors and/or shading to indicate different levels of contamination. The types of contacts, the durations of contacts, the number of times contacted, etc. may be translated to different colors and color saturation levels. As a simple example, highly contaminated surfaces may be in red (and have numerical designators 504), intermediately contaminated surfaces may be in yellow (and have numerical designators 506), and surfaces with low or no contamination may be green (and have numerical designators 508). An infinite range of colors and levels of shading may be provided to illustrate the levels of contamination. Similar views may be provided to show levels of sanitization. For example, poorly cleaned areas or areas that have not been cleaned may be in red, moderately cleaned areas may be in yellow, and thoroughly sanitized areas may be in green. Surfaces that are not observed by cameras, sensors and/or feature activation tracking may be encoded with gray coloring in order to denote system uncertainty of the contamination and/or sanitization states of these surfaces. The activity tracking may include cleaning activities including durations surfaces are cleaned and identifying surfaces and/or portions thereof that have been cleaned, partially cleaned and/or not cleaned. A cleaning mode may be activated to allow displayed markings to be removed as surfaces are cleaned.

As an alternative to showing different colors and/or shading, different values and/or percentages may be displayed indicating contamination levels. This may be based on duration of contact and/or amounts of time being in contact and/or close proximity of the surfaces. Additional information may also be displayed. This may include additional contextual information, such as a location of the vehicle when contacts have occurred. For example, this information may indicate if the vehicle was in a highly polluted area when the contacts were made indicating that the contamination levels of the contacts may be higher than if the contacts were made in a low pollution area. The information may include cleanliness information and/or antimicrobial and/or antiviral surface material indications and/or decay rates.

The portable network device 502 includes an interior facing camera. The vehicle includes sensors and an internal network for tracking states of components and/or devices to track items touched and/or actuated by an occupant to control and/or change state of a vehicle feature. A vehicle feature may refer to a window, door, mirror, lights, information displayed, infotainment features, stereo selections, navigation selections, etc. The vehicle may report the track contact activity to the and/or the contamination information to the portable network device 502, which may then display images with contaminated areas highlighted, as shown. The portable network device 502 may show, as an example, that stereo controls were touched, steering wheel controls were touched, etc. Feature tracking may be performed by any and/or all of the modules 204, 220, 222, 224 of FIG. 2 to identify controls that have come in physical contact with humans. When a specific feature is engaged, it may be inferred that the control required to activate the feature has been touched, unless voice activated. Tracked features may include infotainment controls and screens, primary controls (e.g., steering, gear shifters) wiper controls, window controls, mirror adjustment controls, interior door handles, etc.). Instances of surface contacts and associated locations are recorded from various sources, centrally aggregated and then shared.

Touch points are recorded and aggregated to create a visual map of likely contamination points, which may be viewed using an in vehicle or mobile application. The mobile application includes various views of the interior and also an AR view in which touched surfaces may be viewed with greater detail through a view-finder of the portable network device 502. This may be done to efficiently identify areas to be avoided by passengers of the vehicle.

Figure 6:
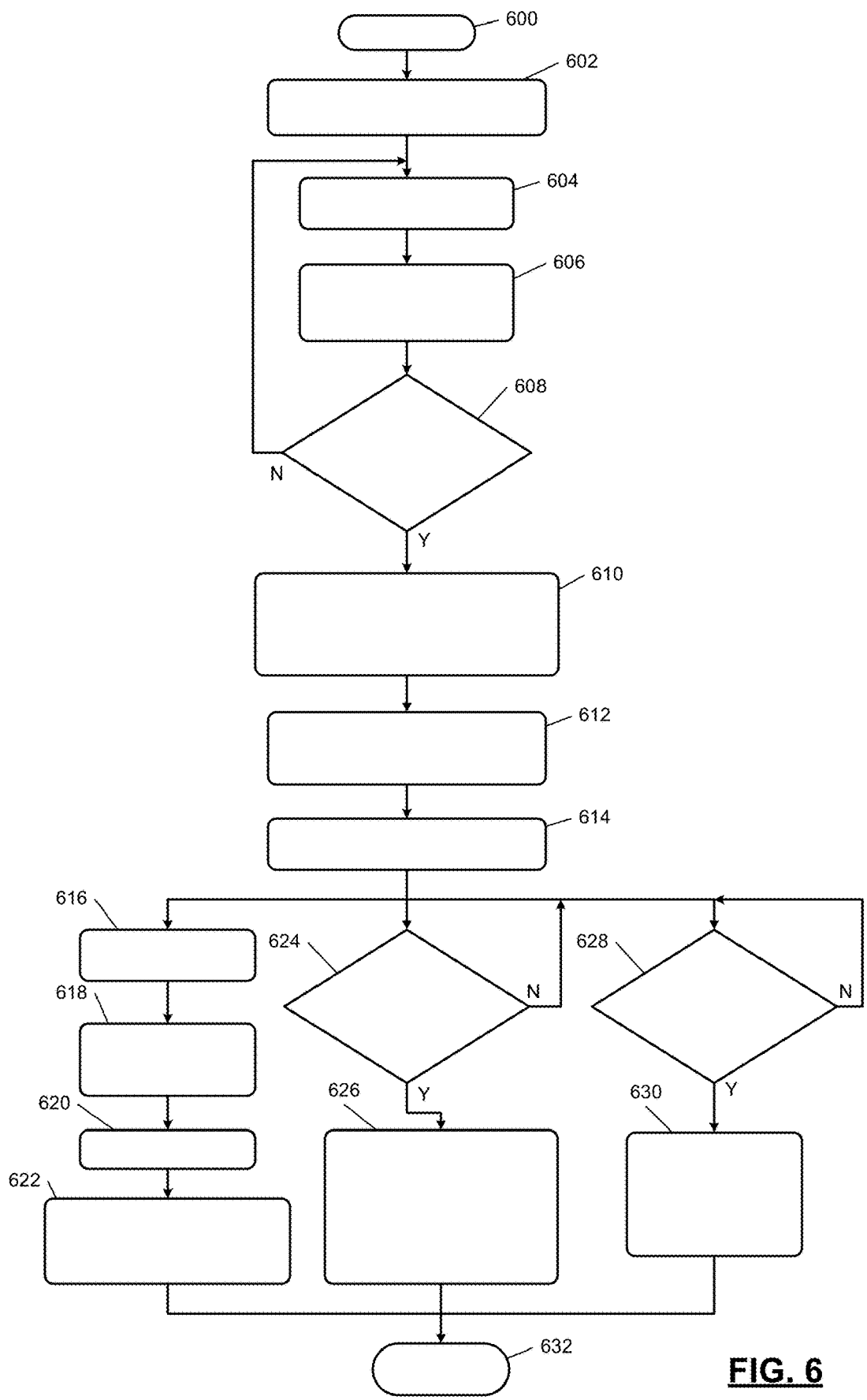
FIG. 6 illustrates a surface contamination indication method in accordance with the present disclosure.

FIG. 6 shows a surface contamination indication method. Although the following operations are primarily described with respect to the implementations of FIGS. 1-3, the operations may be easily modified to apply to other implementations of the present disclosure. The operations may be iteratively performed. The method may begin at 600. At 602, the contamination detection and notification system 201 may be activated and/or initialized. The system 201 may be initialized, for example, when an area being monitored is fully sanitized. All contamination values may be reset to, for example, a null or initial state. As surfaces and/or areas become more and more contaminated, the contamination values may increase.

At 604, the activity tracking module 224 tracks activity based on information received from the sensors 123, 210 and the indicator input devices 125, 208. At 606, the activity tracking module 224 stores the collected activity data and may report the activity data to, for example, the central monitoring station 110.

At 608, the modules 220, 222 may determine whether requests have been received to show a contamination map and/or a sanitization map of a given area. If yes, operation 610 may be performed. For example, a user may start a contamination and/or sanitization application on a portable network device and/or in the vehicle using a vehicle infotainment system.

At 610, the infotainment module 204 may collect and/or receive localization, contamination, sanitization, cleaning, alert, and/or other information from a remote server (e.g., the central monitoring station 110). The modules 220, 222 may convert the activity data to contamination and/or sanitization data, which may include visual data, such as surface location and/or identification information and corresponding contamination and sanitization levels. At 614, the infotainment module 204 may store received and/or generated data, which may include received contamination and/or sanitization levels, in memory 212.

At 616, the infotainment module 204 may generate a report and at 618 display the status report. The status report may indicate the contamination levels, sanitization levels, when surfaces were last contacted, when surfaces were last cleaned, estimated indications of how well the surfaces were cleaned, etc.

At 620, the infotainment module 204 may analyze the report 620 to determine: areas and/or surfaces to stay away from until cleaned; areas and/or surfaces that need cleaning; and/or other status information.

At 622, the infotainment module 204 may generate via one or more of the transceivers 235 alert signals indicating areas of high contamination and/or that need to be cleaned. This allows for efficiencies in cleaning. Areas that need to be cleaned are identified and cleaned, whereas other areas that do not need to be cleaned are avoided. This decreases amounts of time and/or costs associated with cleaning.

At 624, the infotainment module 204 may determine whether a request has been received to show contamination and/or sanitization results. If yes, operation 626 may be performed. At 626, the modules 220, 222 may display contamination and/or sanitization indications and/or indicators. In addition and/or as an alternative the contamination and/or sanitization information may be transmitted to the portable network device 300. The portable network device 300 may then display this information, as described above.

At 628, the infotainment module 204 may determine if a request has been received to operate in a surface indication mode. If yes, operation 630 may be performed. At 630, the infotainment module 204 may display contamination and/or sanitization indications via smart surfaces, as described above. Subsequent to operations 622, 626, 630, the method may end at 632.

As an example implementation, a rideshare passenger may have interest in taking special care when taking a taxi. The rideshare passenger prior to entering the taxi may start a contact tracking application (or AR-enabled contact tracking application) such as that described above on a portable network device. The contact tracking application may be interfaced with a rideshare application, which may also be implemented on the portable network device. The portable network device may contact, for example, a central monitoring station to obtain contamination information associated with the taxi. The passenger may scan via a camera of the portable network device a backseat area of the taxi and see that there has been a high concentration of contact instances of previous passengers around the left-hand side seat and door handle. The passenger may also see that the armrest on that side of the vehicle has not been cleaned for a long time, whereas the right-hand side is shown as having less traffic and contact activity. The passenger may then avoid that area of the back seat and sit on the right-hand side of the backseat. Alternatively, the passenger may clean the armrest and/or other surfaces with, for example, a disinfecting wipe and because of the actions completes the trip with a better piece of mind.

As another implementation example, a retail driver may plan on lending her vehicle to her grandparents while the grandparent's vehicle is being serviced. Due to risks imposed by a pandemic, the retail driver may want to sanitize areas in the vehicle that she or other passengers have previously touched. Before providing the vehicle to her grandparents, she opens the contact tracking application included in an infotainment system of the vehicle and/or on a mobile network device. The contact tracking application may be executed by, for example, one of the modules 204, 220, 224 of FIG. 2. The contact tracking application may then provide contamination and sanitization information via output devices of the vehicle. Based on this information she is able to efficiently locate the contacted surfaces and comprehensively wipe down all of the surfaces and does not have to worry about missing any touched surfaces.

As yet another implementation example, a fleet manager for a company that transports potentially hazardous materials and may institute a new policy that requires drivers to wipe down their vehicles. The fleet manager initiates execution of a contact tracking application via a central monitoring station control module (e.g., the control module 131 of FIG. 1) in order to help enforce this new policy and track cleanliness of the vehicles. The manager is able to centrally monitor the state of the vehicles and reach out to the drivers to improve the cleanliness level and issue reprimands if requested cleaning tasks are not performed. The manager is able to easily view a dashboard overview of the entire vehicle fleet without having to individually investigate each vehicle. The manager is able to see what areas are commonly missed by the drivers and issue informed advice on improved cleaning practices. The manager may feel more comfortable with this system in place due to less potential liability issues. The drivers are happier about the more efficient cleaning afforded to them due to them not having to clean the entire vehicles, but rather only areas that are contaminated and/or have been contacted and/or exposed.

The systems disclosed herein provide data and insights about vehicle use and occupant interactions, identify contaminated areas and suggest targeted cleaning maintenance. Vehicle decontamination guidance is provided based on understanding vehicle usage activities. Analysis of vehicle sensors, vehicle indicator input devices and vehicle hygiene schedules are used to determine hygiene countermeasures.

The above-described operations of FIG. 6 are meant to be illustrative examples. The operations may be performed sequentially, synchronously, simultaneously, continuously, during overlapping time periods or in a different order depending upon the application. Also, any of the operations may not be performed or skipped depending on the implementation and/or sequence of events.

The examples set forth herein includes methods for tracking areas and surfaces that have been contaminated in order to improve cleaning capabilities and ultimately reduce virus transmission. Traditional vehicle sanitization methods, such as that performed by fleet drivers and managers are inherently inefficient without any indication of which areas require attention and which areas do not require attention. The examples disclosed herein use various technologies working in tandem in order to track contamination and sanitization states of points throughout a vehicle interior. The technologies include cameras (e.g., interior facing, exterior facing, visible, near IR and far IR) for image and video recording and evaluation, monitoring of other sensors (e.g., pressure, temperature, proximity, IR, light, microphone, etc.), and feature activation, deactivation and control tracking. Motion tracking is utilized to determine when movements cause passengers to come in physical contact with surfaces and where the contact points are located. This also includes fusing information from the various sensors and devices.

Contact time durations are tracked in order to provide information regarding when potential viral, chemical and radioactive contaminates have likely decayed. This information is also based on the types of materials of the contacted surfaces. Contact instances may be visualized via a mobile application and/or interface (e.g., a digital display in a cockpit, digital rendering of the cockpit, and/or use of AR to highlight touches surfaces when viewed through a camera of a portable network device (e.g., smart glasses). Contact instances may also be visualized via smart surface indications and projectors (e.g., a light projector).

The disclosed systems may be utilized by: passengers (e.g., members of a rideshare program) to avoid contaminated areas; fleet owners to sanitize areas in a more efficient manner by allowing the fleet owners to identify areas that do not require much attention. Collection and analysis of vehicle cleaning events, exposure times with and without occupants, and other collected and determined data is performed. Countermeasures are performed based on vehicle usage data (e.g., scheduled and performed decontamination and maintenance while providing enhanced alerts based on vehicle functions performed. Data and insights are provided about vehicle use and occupant interactions as well as suggesting targeted cleaning maintenance. Countermeasures may be implemented such as providing contamination alerts, cleaning alerts, and information alerts. The countermeasures may include automatic cleaning and/or disinfecting of areas, such as the injection and/or spraying of disinfectant in the areas. The countermeasures are applied based on vehicle usage data granularity (e.g., schedule, vehicle decontamination or maintenance, enhanced alerts based on vehicle function, etc.).

The foregoing description is merely illustrative in nature and is in no way intended to limit the disclosure, its application, or uses. The broad teachings of the disclosure can be implemented in a variety of forms. Therefore, while this disclosure includes particular examples, the true scope of the disclosure should not be so limited since other modifications will become apparent upon a study of the drawings, the specification, and the following claims. It should be understood that one or more steps within a method may be executed in different order (or concurrently) without altering the principles of the present disclosure. Further, although each of the embodiments is described above as having certain features, any one or more of those features described with respect to any embodiment of the disclosure can be implemented in and/or combined with features of any of the other embodiments, even if that combination is not explicitly described. In other words, the described embodiments are not mutually exclusive, and permutations of one or more embodiments with one another remain within the scope of this disclosure.

Spatial and functional relationships between elements (for example, between modules, circuit elements, semiconductor layers, etc.) are described using various terms, including "connected," "engaged," "coupled," "adjacent," "next to," "on top of," "above," "below," and "disposed." Unless explicitly described as being "direct," when a relationship between first and second elements is described in the above disclosure, that relationship can be a direct relationship where no other intervening elements are present between the first and second elements, but can also be an indirect relationship where one or more intervening elements are present (either spatially or functionally) between the first and second elements. As used herein, the phrase at least one of A, B, and C should be construed to mean a logical (A OR B OR C), using a non-exclusive logical OR, and should not be construed to mean "at least one of A, at least one of B, and at least one of C."

In the figures, the direction of an arrow, as indicated by the arrowhead, generally demonstrates the flow of information (such as data or instructions) that is of interest to the illustration. For example, when element A and element B exchange a variety of information but information transmitted from element A to element B is relevant to the illustration, the arrow may point from element A to element B. This unidirectional arrow does not imply that no other information is transmitted from element B to element A. Further, for information sent from element A to element B, element B may send requests for, or receipt acknowledgements of, the information to element A.

In this application, including the definitions below, the term "module" or the term "controller" may be replaced with the term "circuit." The term "module" may refer to, be part of, or include: an Application Specific Integrated Circuit (ASIC); a digital, analog, or mixed analog/digital discrete circuit; a digital, analog, or mixed analog/digital integrated circuit; a combinational logic circuit; a field programmable gate array (FPGA); a processor circuit (shared, dedicated, or group) that executes code; a memory circuit (shared, dedicated, or group) that stores code executed by the processor circuit; other suitable hardware components that provide the described functionality; or a combination of some or all of the above, such as in a system-on-chip.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

The term code, as used above, may include software, firmware, and/or microcode, and may refer to programs, routines, functions, classes, data structures, and/or objects. The term shared processor circuit encompasses a single processor circuit that executes some or all code from multiple modules. The term group processor circuit encompasses a processor circuit that, in combination with additional processor circuits, executes some or all code from one or more modules. References to multiple processor circuits encompass multiple processor circuits on discrete dies, multiple processor circuits on a single die, multiple cores of a single processor circuit, multiple threads of a single processor circuit, or a combination of the above. The term shared memory circuit encompasses a single memory circuit that stores some or all code from multiple modules. The term group memory circuit encompasses a memory circuit that, in combination with additional memories, stores some or all code from one or more modules.

The term memory circuit is a subset of the term computer-readable medium. The term computer-readable medium, as used herein, does not encompass transitory electrical or electromagnetic signals propagating through a medium (such as on a carrier wave); the term computer-readable medium may therefore be considered tangible and non-transitory. Non-limiting examples of a non-transitory, tangible computer-readable medium are nonvolatile memory circuits (such as a flash memory circuit, an erasable programmable read-only memory circuit, or a mask read-only memory circuit), volatile memory circuits (such as a static random access memory circuit or a dynamic random access memory circuit), magnetic storage media (such as an analog or digital magnetic tape or a hard disk drive), and optical storage media (such as a CD, a DVD, or a Blu-ray Disc).

The apparatuses and methods described in this application may be partially or fully implemented by a special purpose computer created by configuring a general purpose computer to execute one or more particular functions embodied in computer programs. The functional blocks, flowchart components, and other elements described above serve as software specifications, which can be translated into the computer programs by the routine work of a skilled technician or programmer.

The computer programs include processor-executable instructions that are stored on at least one non-transitory, tangible computer-readable medium. The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc.

The computer programs may include: (i) descriptive text to be parsed, such as HTML (hypertext markup language), XML (extensible markup language), or JSON (JavaScript Object Notation) (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Swift, Haskell, Go, SQL, R, Lisp, Java®, Fortran, Perl, Pascal, Curl, OCaml, Javascript®, HTML5 (Hypertext Markup Language 5th revision), Ada, ASP (Active Server Pages), PHP (PHP: Hypertext Preprocessor), Scala, Eiffel, Smalltalk, Erlang, Ruby, Flash®, Visual Basic®, Lua, MATLAB, SIMULINK, and Python®.

What is claimed is:

1. A notification system comprising:
  a memory configured to store an activity history log associated with a supporting structure, wherein the supporting structure is an interior structure of a vehicle or a room of a building;
  an activity module configured to
    receive a plurality of signals from at least one of sensors or electrical devices of the supporting structure, and
    track activities at least one of in or within set distances of surfaces of the supporting structure to generate the activity history log;
  a localization module configured to relate the activities to aspects of the supporting structure and generate corresponding localization data, wherein the aspects are within the supporting structure and include at least one of surfaces, areas, spaces or volumes of the supporting structure;
  a tracking module configured to i) track states of the aspects of the supporting structure contacted by one or more animate objects and contaminated due to the contact by the one or more animate objects, ii) determine at least one of a plurality of contamination levels or a plurality of sanitization levels of the aspects based on the localization data and the activity history log, and iii) track decay of the plurality of contamination levels and adjust the plurality of contamination levels based on the decay; and
  an output device configured to indicate the at least one of the plurality of contamination levels or the plurality of sanitization levels, and indicate the plurality of contamination levels as adjusted based on the decay.

2. The notification system of claim 1, further comprising a transceiver configured to receive a notification key indicating a network device has been identified as being exposed to a contaminant,
  wherein the tracking module configured to, in response to the notification key, track the aspects of the supporting structure contacted by the one or more animate objects and determine the at least one of the plurality of contamination levels or the plurality of sanitization levels of the aspects based on the localization data and the activity history log.

3. The notification system of claim 1, further comprising sensors configured to detect activities in the supporting structure, wherein the activity module is configured to track the activities based on outputs of the sensors.

4. The notification system of claim 1, further comprising the electrical devices configured to change state as a result of activities in the supporting structure, wherein the activity module is configured to track states of the electrical devices and log the states in the activity history log.

5. The notification system of claim 1, further comprising one or more cameras configured to track activities of the one or more animate objects, wherein:
  the interior structure is of the vehicle;
  the output device is at least one of a display of the vehicle or one or more smart aspects of the vehicle; and
  the activity module is configured to determine aspects of the supporting structure contacted based on outputs of the one or more cameras and log the aspects contacted and corresponding timestamps in the activity history log.

6. The notification system of claim 1, wherein the activity module is configured to track touch points of the one or more animate objects and log the touch points and corresponding timestamps in the activity history log.

7. The notification system of claim 1, wherein:
  the output device is at least one of a display or a projector; and
  the output device is configured to at least one of
    highlight areas of the supporting structure in an image shown on the display to illustrate the at least one of the plurality of contamination levels or the plurality of sanitization levels of the aspects, or
    project images on the aspects of the supporting structure to indicate the at least one of the plurality of contamination levels or the plurality of sanitization levels of the aspects.

8. The notification system of claim 1, wherein the tracking module is configured to identify aspects contacted based on detected changes in states of the electrical devices and update the at least one of the plurality of contamination levels or the plurality of sanitization levels based on the identified aspects contacted.

9. The notification system of claim 1, further comprising sensors configured to detect at least one of breathing, coughing or sneezing by the one or more animate objects,
wherein the tracking module is configured to, based on the detected at least one of the breathing, coughing or sneezing, update the at least one of the plurality of contamination levels or the plurality of sanitization levels.

10. The notification system of claim 1, wherein:
the activity module is configured to track number of times each of the aspects are contacted and durations of contacts with the aspects; and
the tracking module is configured to update the at least one of the plurality of contamination levels or the plurality of sanitization levels based on the number of times each of the aspects are contacted and the durations of the contacts with the aspects.

11. The notification system of claim 1, further comprising a transceiver configured to transmit the activity history log to a server and receive in response a cleaning notification message indicating at least one of areas or aspects of the supporting structure to sanitize.

12. The notification system of claim 1, wherein the activity module performs motion tracking of the animate objects and determines incidents in which physical contact is made with interior aspects of the supporting structure and updates the activity history log based on the physical contacts made.

13. The notification system of claim 1, further comprising embedded sensors configured to detect contact with the aspects,
wherein the activity module is configured to update the activity history log based on outputs of the embedded sensors.

14. A portable network device comprising:
a camera configured to capture images of a supporting structure;
a memory configured to store localization data, wherein the localization data relates location and orientation of the portable network device to aspects of the supporting structure, wherein the aspects include at least one of surfaces, areas, spaces or volumes of the supporting structure, and wherein the supporting structure is separate from the portable network device; and
a control module configured to
receive at least one of
an activity history log of activity of one or more animate objects in association with the supporting structure;
a contamination map of contamination levels of the aspects of the supporting structure; or
sanitization map of sanitization levels of the aspects of the supporting structure; and
based on the captured images, display an image of the supporting structure indicating at least one of the contamination levels of the aspects or the sanitization levels of the aspects.

15. The portable network device of claim 14, the control module is configured to i) determine a location and orientation of the portable network device within the supporting structure, ii) based on the location and orientation, display in an augmented reality environment view of an interior of the supporting structure selected ones of the aspects, and iii) based on corresponding ones of the contamination levels of the aspects and corresponding ones of the sanitization levels of the aspects highlight the selected ones of the aspects in the augmented reality environment view of the interior of the supporting structure.

16. The portable network device of claim 14, further comprising a view-finder module configured to determine a relationship between a live view seen by the camera and the at least one of the contamination map or the sanitization map,
wherein the control module is configured to operate in an augmented reality mode and provide a view of an interior of the supporting structure highlighting the aspects in the view based on the at least one of the contamination levels of the aspects or the sanitization levels of the aspects.

17. The portable network device of claim 14, wherein:
the supporting structure is an interior structure of a vehicle or a room of a building;
the aspects are within the supporting structure; and
the contamination levels indicate amounts of contamination of the aspects of the supporting structure due to contact of the aspects of the supporting structure by the one or more animate objects.

18. The portable network device of claim 14, wherein:
the aspects include surfaces within a vehicle or a building; and
the control module is configured to receive at least one of
i) the contamination map including contamination levels of the surfaces, and ii) the sanitization map including sanitization levels of the surfaces.

19. The portable network device of claim 18, wherein the control module is configured to i) receive the contamination map and the sanitization map, and ii) display the image of the supporting structure indicating the contamination levels of the contamination map and the sanitization levels of the sanitization map.

20. A notification system comprising:
a memory configured to store an activity history log associated with a supporting structure, wherein the supporting structure is an interior structure of a vehicle or a room of a building;
an activity module configured to
receive a plurality of signals from at least one of sensors or electrical devices of the supporting structure, and
track activities at least one of in or within set distances of surfaces of the supporting structure to generate the activity history log;
a localization module configured to relate the activities to aspects of the supporting structure and generate corresponding localization data, wherein the aspects are within the supporting structure and include at least one of surfaces, areas, spaces or volumes of the supporting structure;
a tracking module configured to i) track states of the aspects of the supporting structure contacted by one or more animate objects and contaminated due to the contact by the one or more animate objects, and ii) determine at least one of a plurality of contamination levels or a plurality of sanitization levels of the aspects based on the localization data and the activity history log; and an output device configured to indicate the at least one of the plurality of contamination levels or the plurality of sanitization levels,
wherein
the output device includes a smart surface that changes in at least one of a color or an amount of shading, and
the smart surface changes the at least one of the color or amount of shading to indicate the at least one of the plurality of contamination levels or the plurality of sanitization levels.

* * * * *